United States Patent
Yu et al.

(10) Patent No.: US 12,102,285 B2
(45) Date of Patent: Oct. 1, 2024

(54) SURGICAL ROBOTIC TOOL MULTI-MOTOR ACTUATOR AND CONTROLLER

(71) Applicant: Verb Surgical Inc., Santa Clara, CA (US)

(72) Inventors: Haoran Yu, Sunnyvale, CA (US); Renbin Zhou, Wellington, FL (US); Sina Nia Kosari, Fremont, CA (US); Andrea Bajo, Palo Alto, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/184,458

(22) Filed: Mar. 15, 2023

(65) Prior Publication Data

US 2023/0284871 A1 Sep. 14, 2023

Related U.S. Application Data

(63) Continuation of application No. 17/362,871, filed on Jun. 29, 2021, now Pat. No. 11,607,108, which is a
(Continued)

(51) Int. Cl.
*G05B 11/01* (2006.01)
*A61B 1/00* (2006.01)
(Continued)

(52) U.S. Cl.
CPC ........ *A61B 1/00006* (2013.01); *A61B 1/0016* (2013.01); *A61B 1/05* (2013.01);
(Continued)

(58) Field of Classification Search
CPC ......... H02P 5/56; H02P 21/18; A61B 1/00006
See application file for complete search history.

(56) References Cited

U.S. PATENT DOCUMENTS 7,348,751 B2 3/2008 Kawai et al.
8,058,823 B2 11/2011 Horst et al.
(Continued)

FOREIGN PATENT DOCUMENTS

CN 102028548 A 4/2011
CN 105050528 A 11/2015
(Continued)

OTHER PUBLICATIONS

A System for Speed and Torque Control of DC Motors with Application to Small Snake Robots, by Ankur Kapoor, Nabil Simaan, Peter Kazanzides; Department of Computer Science, Johns Hopkins University; 2004; 6 Pages.
(Continued)

*Primary Examiner* — Erick D Glass
(74) *Attorney, Agent, or Firm* — Aikin & Gallant, LLP

(57) ABSTRACT

A first input coupling and a second input coupling are coupled to rotatably drive an output coupling at the same time. In one embodiment, the output coupling rotates a robotic surgery endoscope about a longitudinal axis of the output coupling. A first motor drives the first input coupling while being assisted by a second motor that is driving the second input coupling. A first compensator produces a first motor input based on a position error and in accordance with a position control law, and a second compensator produces a second motor input based on the position error and in accordance with an impedance control law. In another embodiment, the second compensator receives a measured torque of the first motor. Other embodiments are also described and claimed.

20 Claims, 5 Drawing Sheets

Related U.S. Application Data continuation of application No. 15/959,106, filed on Apr. 20, 2018, now Pat. No. 11,071,441.

(51) Int. Cl.

| | | |
|---|---|---|
| *A61B 1/05* | (2006.01) | |
| *A61B 1/313* | (2006.01) | |
| *A61B 17/29* | (2006.01) | |
| *A61B 34/30* | (2016.01) | |
| *H02P 5/56* | (2016.01) | |
| *H02P 21/18* | (2016.01) | |
| *A61B 17/00* | (2006.01) | |

(52) U.S. Cl.
CPC ............ *A61B 1/3132* (2013.01); *A61B 17/29* (2013.01); *A61B 34/30* (2016.02); *H02P 5/56* (2016.02); *H02P 21/18* (2016.02); *A61B 2017/00398* (2013.01); *A61B 2034/301* (2016.02)

(56) References Cited

U.S. PATENT DOCUMENTS

| | | | |
|---|---|---|---|
| 8,727,736 B2 | 5/2014 | Walth | |
| 2007/0287992 A1* | 12/2007 | Diolaiti | A61B 34/71 606/1 |
| 2011/0015650 A1 | 1/2011 | Choi et al. | |
| 2011/0290125 A1 | 12/2011 | Ito et al. | |
| 2011/0290126 A1 | 12/2011 | Ito et al. | |
| 2012/0215357 A1* | 8/2012 | Igarashi | B25J 13/088 901/46 |
| 2015/0100065 A1 | 4/2015 | Zinn | |
| 2016/0015937 A1 | 1/2016 | Hart et al. | |
| 2016/0039093 A1 | 2/2016 | Abdallah et al. | |
| 2016/0221129 A1* | 8/2016 | Taagepera | B23P 6/00 |
| 2017/0014998 A1 | 1/2017 | Langenfeld et al. | |
| 2017/0172549 A1 | 6/2017 | Smaby et al. | |
| 2017/0172672 A1 | 6/2017 | Bailey et al. | |
| 2017/0340397 A1 | 11/2017 | Smaby et al. | |
| 2019/0345959 A1 | 11/2019 | Tanaka et al. | |
| 2020/0054403 A1 | 2/2020 | Zhou et al. | |

FOREIGN PATENT DOCUMENTS

| | | |
|---|---|---|
| KR | 10-2016-0140843 A | 12/2016 |
| WO | 2014/154529 A1 | 10/2014 |
| WO | 2014/172208 A1 | 10/2014 |
| WO | 2015/153636 A1 | 10/2015 |

OTHER PUBLICATIONS

Extended European Search Report from related European Application No. 18915369.5, dated Dec. 15, 2021 (9 pages).

Fundamentals of Servo Motion Control, by David Kaiser; Parker Hannifin—Electromechanical Automation Div./800-358-9070/ 2007; 12 Pages; <www.parkermotion.com>.

Impedance Control of Robots Using Voltage Control Strategy, by Mohammad Mehdi Fateh, Reza Babaghasabha; Springer Science+ Business Media Dordrecht, Nonlinear Dynamics 2013, vol. 74, Issue 1-2, pp. 277-286.

PCT International Preliminary Report on Patentability dated Oct. 20, 2020, for related PCT Appln. No. PCT/US18/031284 11 Pages.

PCT Search Report and Written Opinion dated Jan. 1, 2019, for related PCT Appln. No. PCT/US18/031284 11 Pages.

Torque and Speed Control of DC-Servomotors for Robots, by Yoram Koren, S. Malkin; Annals of the CIRP vol. 33, issue 1; 1984; pp. 239-242.

Office Action received for Chinese Patent Application No. 201880092567.2, mailed on Nov. 20, 2023, 20 pages (11 pages of English Translation and 9 pages of Original Document).

* cited by examiner

SURGICAL ROBOTIC TOOL MULTI-MOTOR ACTUATOR AND CONTROLLER

This application is a continuation of U.S. application Ser. No. 17/362,871, filed Jun. 29, 2021, entitled "Surgical Robotic Tool Multi-Motor Actuator And Controller," which application is a continuation of U.S. application Ser. No. 15/959,106, filed on Apr. 20, 2018, now U.S. Pat. No. 11,071,441, issued Jul. 27, 2021, which are incorporated herein by reference in their entirety to provide continuity of disclosure.

FIELD

An embodiment of the invention relates to electro-mechanical control systems for motion control of a robotic surgery endoscope. Other embodiments are also described.

BACKGROUND

Robotic surgery systems give an operating surgeon greater dexterity, and they may also enable the surgeon to perform the operation from a remote location. In a robotic surgery system, a surgical tool or instrument is mechanically coupled to a robot joint, so that movement or actuation of the robot joint directly causes a rotation, pivoting or linear movement of a part of the tool (e.g., rotation of an endoscope camera, pivoting of a grasper jaw, or translation of a needle.) Such movement is achieved and controlled by an electro-mechanical feedback control system. The control system receives a joint command or joint setpoint, e.g., a desired "position" of a joint, meaning its position or orientation. The joint command may have been generated by a robotic surgery computer program, based on and representing a higher layer command received from a computerized user interface such as a joystick that is being manipulated by the surgeon. The control system then actuates the robot joint in accordance with the joint command.

The control system includes a tool drive, in which there are one or more actuators. Each actuator has a respective electric motor (e.g., a brushless permanent magnet dc motor) whose drive shaft may be coupled to a respective actuator output shaft or drive disk through a transmission (e.g., a gear train that achieves a given gear reduction ratio.) The drive disk is designed to mechanically engage a mating disk that is in the tool or instrument (when the instrument has been coupled to the tool drive.) A motor driver circuit manipulates the electrical power drawn by the motor in order to regulate the speed of the motor or its torque, in accordance with a motor driver circuit input. A digital, control system compensation controller translates the joint command into the motor driver circuit input, using position feedback from the joint, so as to track the changing joint command.

SUMMARY

A robotic surgery tool such as a rotatable endoscopic digital video camera presents a particular form of mechanical resistance or load to the coupled tool drive joint, namely the twisting of an electrical camera cable. The cable provides power to and acts as a video communication link for the camera. The actuator in such a tool drive needs to have sufficient torque to overcome such resistance. In addition, the actuator should have a compact profile to allow the tool to be used simultaneously with other tools that are being used to operate upon a patient. The electro-mechanical feedback control system of which the actuator is a part has a digital controller which serves to close the feedback control loop, and needs to do so in a way that ensures command tracking (position of the tool drive joint) and disturbance rejection, while reducing parameter sensitivity. The solution as a whole should also be reliable and durable, especially when it is part of a robotic surgery system.

An embodiment of the invention is a multi-motor actuator and controller for a robotic surgery tool, for use as part of a control system that tracks a joint command that has been received for the surgery tool. The actuator has at least two input shafts that are coupled through a transmission to simultaneously and rotatably drive an output shaft (the latter being configured to be coupled to a surgery tool, such as an endoscope.) Each input shaft is actuated by a respective motor subsystem. A controller determines a position error based on a difference between a position input and a position feedback, and on that basis produces the appropriate motor subsystem inputs. The position feedback may be on any one of the input shafts (relates to or gives feedback on the position of the input shaft) or on the output shaft, and is understood as referring to the position input which is being tracked by the control system. The controller produces a first motor subsystem input based on the position error and in accordance with a position control law. The first motor subsystem may be described as the primary motor subsystem. At the same time, the controller is producing a second motor subsystem input also based on the position error, but in accordance with an impedance control law (the latter using a velocity variable that is obtained either from the position input or as feedback on the first input shaft, the second input shaft, or the output shaft.) In this manner, the second motor subsystem, which may be described as a secondary motor subsystem, provides torque assist to the primary motor subsystem to overcome the resistance of the load on the output shaft (e.g., a twisting endoscope camera cable, friction and inertia of the endoscope camera), thereby improving the tracking performance. There may be more than one secondary motor subsystem whose torque is being summed, together with that of the primary motor subsystem, at the output shaft.

A torque feedforward path may be added to the compensation scheme that is used to compute the inputs for any one or more of the motor subsystems, to compensate for friction and backlash especially when the position input is changing direction, to help maintain accuracy.

To help avoid the shock when backlash is suddenly overcome, a further feedforward path may be added to the input of a secondary motor subsystem. This may ensure that during backlash, the velocity of the associated output shaft is high enough but as soon as backlash has been overcome the torque on the associated output shaft is reduced.

In another embodiment, the controller produces a primary motor subsystem input based on the position error and in accordance with a position control law, but the impedance control law is not used for controlling the secondary motor subsystems. Instead, the controller produces the secondary motor subsystem input differently, by measuring motor current of the first motor subsystem and then low pass filtering the measured motor current before performing a control system compensation scheme upon it, to produce the second motor subsystem input. This approach may also improve the balancing of the workload between the primary and secondary motor subsystems.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

Figure 1:
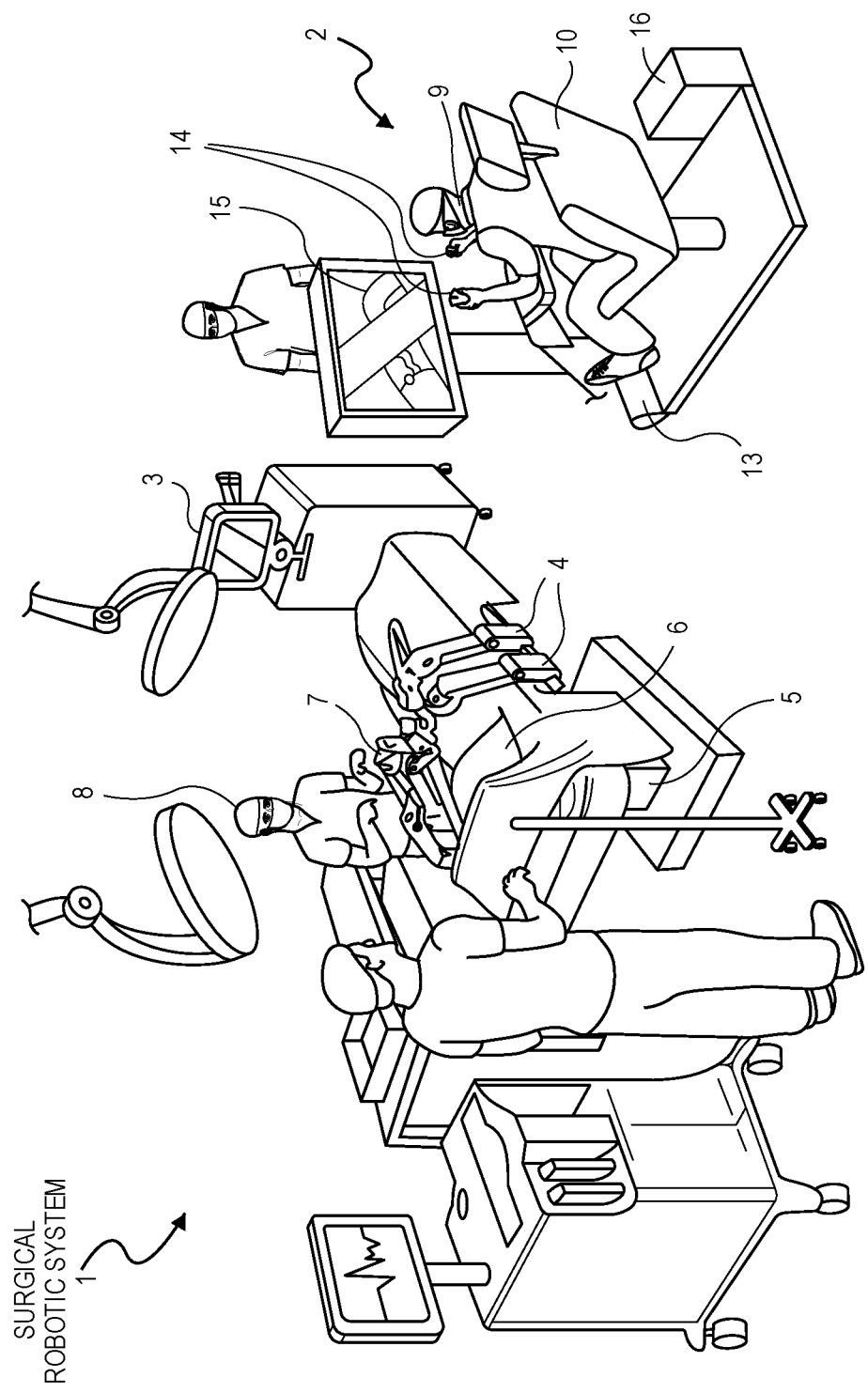
FIG. 1 is a pictorial view of an example surgical robotic system in an operating arena

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The robotic surgical system 1 can incorporate any number of devices, tools, or accessories used to perform surgery on a patient 6. For example, the robotic surgical system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the robotic surgical system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the surgical robotic system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the surgical robotic system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

Robotic surgical system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right surgical arm 4 that is secured to the bed or table to the right side of the patient, and a left surgical arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the surgical robotic platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
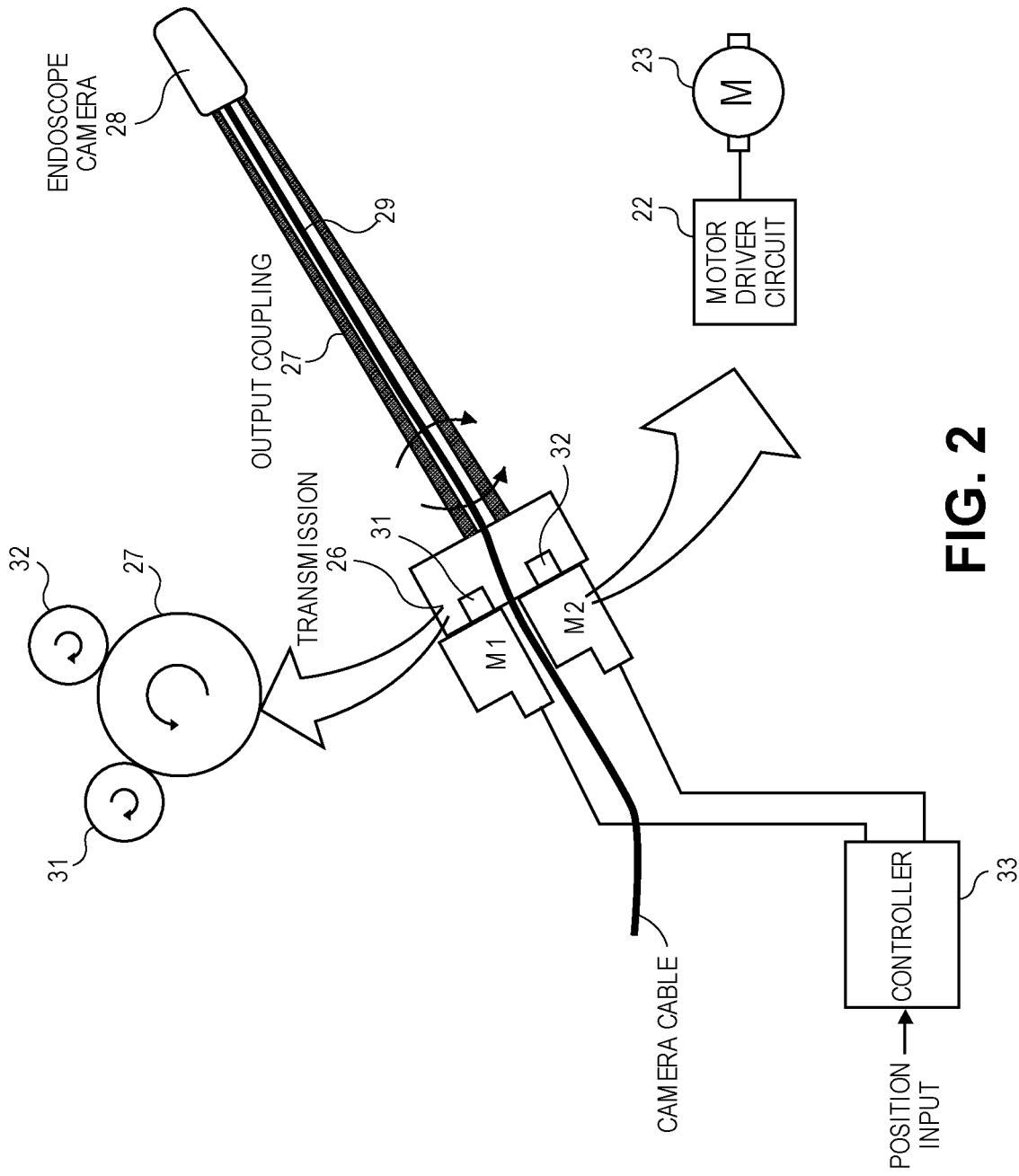
FIG. 2 depicts a multi-motor actuator and controller for a surgery tool.

FIG. 2 depicts a multi-motor actuator and controller for a surgery tool. The actuator has a first motor subsystem M1 and a second motor subsystem M2, where these are also referred to here as a primary motor subsystem M1 and a secondary motor subsystem M2. Each motor subsystem includes a respective solid-state motor driver circuit 2 that is configured to manipulate power (e.g., electrical power) drawn by a respective motor 23, and in accordance with a motor subsystem input (e.g., an analog or digital command voltage that represents a desired motor torque or motor speed and a desired direction or rotation.) The inputs to the motor subsystems are produced by a digital controller 33 (to be described further below.) The motor 23 may be a permanent magnetic brushless DC motor, or another type of motor that is suitable for actuating a surgery tool. The drive coupling of each motor 23 is coupled to rotate a respective input coupling, here first input coupling 31 and second input coupling 32. An example of a coupling is a shaft. Although not shown, there may be a transmission that couples the drive couplings of the motor subsystems M1, M2 to their respective input couplings 31, 32, for example through a respective gear train (without a belt or chain or other similar flexible coupling.) To produce increased torque at the input coupling, the transmissions should effectuate a gear reduction from the motor drive coupling to its respective input coupling.

The motor subsystems M1, M2 may be replicates, in order to reduce the complexity of manufacturing the system as a whole that is shown. However, given that a controller 33, which computes the inputs to M1, M2 as described below, effectively decouples the dynamics of the two motor subsystems and their transmissions from each other, the motor subsystems M1, M2 need not be replicates in that they may have different dynamic properties (e.g., inertia, friction, and backlash.)

Each input coupling is coupled to rotatably drive an output coupling 27 at the same time, through a transmission 26, so that the torques produced by the several motor subsystems are summed at the output coupling 27. FIG. 2 depicts an example where the transmission 26 includes a gear reduction, when summing the torques. In one embodiment, transmission 26 is a direct gear drive (rigid coupling) that couples the input couplings 31, 32 to rotatably drive the output coupling 27 simultaneously. In other embodiments, the transmission 26 may include a flexible coupling, for example a belt or a cable that couples the input couplings 31, 32 to the output coupling 27. In addition, there may be more than one secondary motor subsystem M2 that, as explained below, is assisting the primary subsystem M1 to meet the torque demand on the output coupling 27. In that case, the transmission 26 may have a more complicated design that is able to sum the torques produced by the subsystem M1 and by two or more subsystems M2 (at the output coupling 27.)

In the example depicted in FIG. 2, the output coupling 27 is part of a surgical robotic endoscope. It is rigid and elongated, extending along its longitudinal axis 29 from a proximal point where it joins the transmission 26, to a distal point at which an endoscope camera 28 is coupled to rotate as one with the output coupling 27. Thus, rotation of the output coupling 27 results in direct rotation of the endoscope camera 28, about the axis 29. A camera cable has been passed through a hollow in the output coupling 27 as shown, reaching the distal end where it connects to the camera 28, providing power to and acting as a video communication link to the camera 28. It can be seen that rotation of the output coupling 27, which is needed to rotate the field of view of the camera 28, will result in the twisting of the camera cable thereby increasing the resistance on the output coupling 27 that has to be overcome by the torque produced by the combination of the primary and secondary motor subsystems M1, M2.

Figure 3:
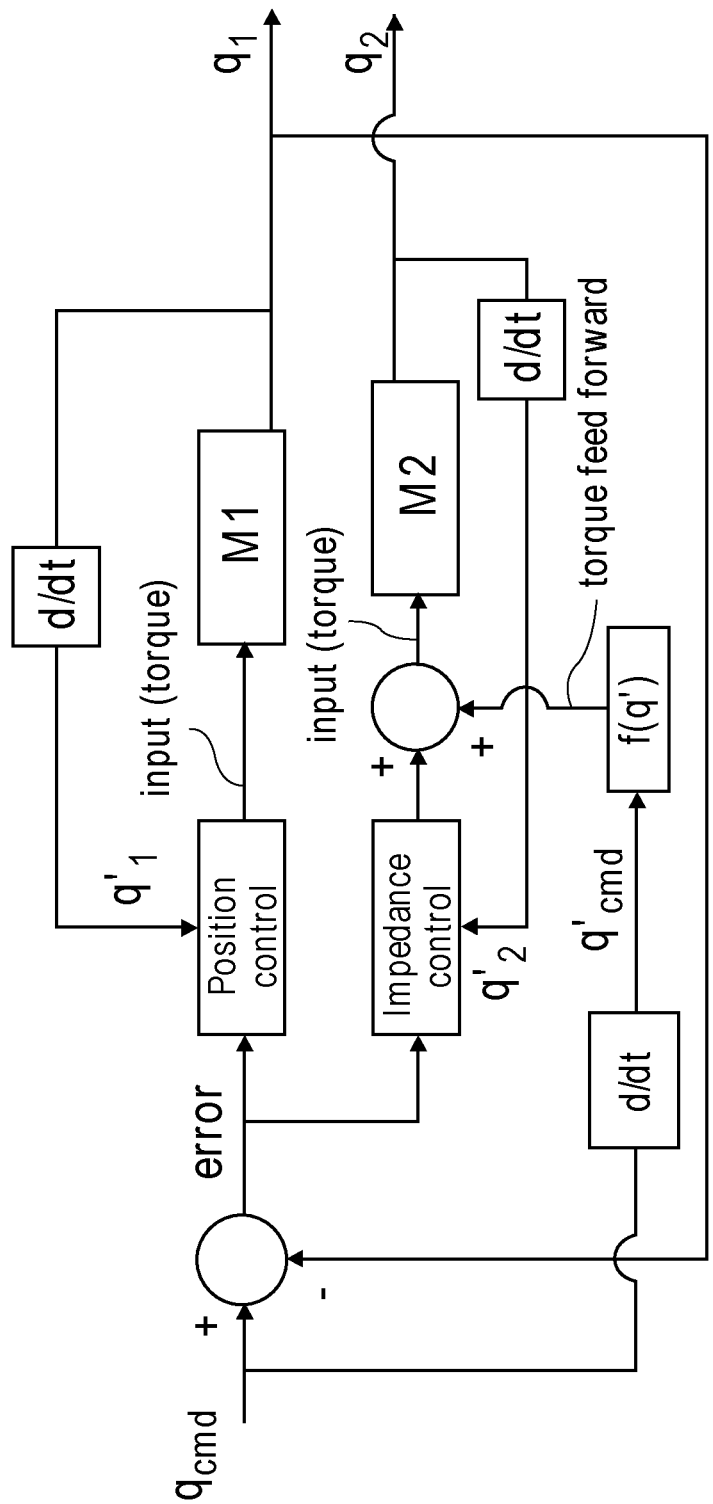
FIG. 3 is a block diagram showing an embodiment of the controller.

The inputs to the motor subsystems M1, M2 are time-varying values produced by the controller 33 so that the output coupling 27 tracks a time-varying position command, using feedback about the actual position of the output coupling 27 (as obtained by a position encoder, for example.) The position input may also be referred to here as a joint command, which indicates a desired or target position of the joint being actuated, for example the output coupling 27. Alternatively, and as depicted in the embodiments of FIG. 2 and FIG. 3 described below, the position input (referred to as qcmd in FIG. 2 and FIG. 3) may refer to the position of the input coupling 31 or the input coupling 32. For example, the position input may refer to the position of the output coupling 27, but a position encoder may not be available on the output coupling 27. Rather, the position encoder may be located on the output coupling 31, and this is acceptable if the mechanical transmission or relationship between rotation of the input coupling 31 and rotation of the output coupling 27 is known, e.g., a fixed gear ratio. Thus, if for example the position input indicates that the output coupling 27 should rotate clockwise by 30 degrees, then the known relationship through the transmission 26 (stored for example as gear ratio data in the controller 33) may be used to translate this position input from the "domain" of the output coupling 27 into the domain of the input coupling 31, e.g., rotate counterclockwise by 90 degrees, and into the domain of the input coupling 32, e.g., rotate counterclockwise by 180 degrees.

Turning now to FIG. 3, this is a block diagram of one embodiment of the controller 33, which serves to close the feedback control loop that is shown. The controller 33 may be a digital or sampled data system that is part of several feedback control loops, which are producing updates to the primary and secondary motor subsystem inputs q1 (position) and q2 (position) on a per sample basis, in order to achieve command tracking (position of a joint) and disturbance rejection, while reducing sensitivity to errors that may inevitably be made when modeling the parameters of the actuator (containing subsystems M1, M2.) Such parameters (e.g., motor torque constant, motor inertia, and friction) are used in two compensator blocks (position control and impedance control) which produce the inputs to the two motor subsystems M1, M2 (here, as torque commands or torque inputs.)

The controller 33 determines a position error (error) which may be a computed difference between a position input (qcmd) and a corresponding position feedback, whereas discussed above the position feedback may for example be derived from the output of a position encoder that is located on the first input coupling 31, the second input coupling 32, or the output coupling 27.

In the embodiment of FIG. 3, a first compensator (position control) produces the first motor subsystem input (input M1 torque) based on the position error and in accordance with a position control law. The first compensator (position control) may use a first velocity variable that is obtained i) from the position input or ii) as feedback from a position encoder that is on the first input coupling, the second input coupling, or the output coupling. The first compensator can be described as being in an "outer control loop."

Running simultaneously with the first compensator is a second compensator (impedance control) that is producing the second motor subsystem input (input M2 torque) based on the position error and in accordance with an impedance control law. Here, the second compensator (impedance control) uses a velocity variable to achieve the goal of impedance control. This velocity variable may be obtained i) from the position input or ii) as feedback from a position encoder on one of the first input coupling 31, the second input coupling 32, or the output coupling 27; in the example shown in FIG. 2, the velocity variable used in the second compensator (impedance control law) is obtained as feedback on the second input coupling 32, e.g., by computing the time derivative d/dt of the sampled position variable q2 (this is indicated in the drawings as q2'). An additional input to the second compensator is the position error. The second compensator (impedance control) can be described as being in an "inner control loop" which may have a higher control bandwidth than the outer control loop that includes the first compensator (position control).

In the particular example shown in FIG. 3, the first compensator for the position control law includes a proportional-integral-derivative, PID, compensator, and the second compensator that implements the impedance control law includes a proportional-derivative, PD, compensator. Also, the first velocity variable used in a derivative (D) term of the PID compensator is obtained as feedback from a position encoder on the first input coupling 31, and the second velocity variable used in a derivative (D) term of the PD compensator is obtained as feedback from a position encoder on the second input coupling 32.

In one embodiment, each of the primary and secondary motor subsystems is undersized in that its respective motor torque rating is insufficient to drive the output coupling by itself through the transmission 26. For example, the motor current of M1 or M2 can saturate, or the motor will stall, if it is driving the output coupling 27 by itself through the transmission 26. Accordingly, during operation of this version of the embodiment of FIG. 3, the error may initially increase because M1 is not strong enough. As the error is also used by the second compensator, to compute a torque or motor current input to M2, the larger the error, the more torque is input (commanded) to M2. This then causes the error to become smaller. This type of swing in the error may be symptomatic of a stability issue in the way in which the M2 motor torque is controlled. The second velocity variable (feedback from the second input coupling 32, or q2') may be used to stabilize the M2 torque loop, by adding damping, e.g., configuring the second compensator as a PD controller having an output given as Kp*error−Kd*q2' where Kp is the proportional term.

In one embodiment, when the error starts to change but is still "small" or less than a given threshold, the second compensator by itself might not compute a large enough torque input to M2 that can overcome the built-in friction of M2 (e.g., sufficient to start rotation of the input coupling 32.) To address such an issue, FIG. 3 shows as an optional item as the addition of a torque feedforward path which boosts the input M2 torque whenever the position input (qcmd) starts to change, so as to overcome the inherent friction and backlash (e.g., gear train play) in M2. This allows the input coupling 32 to begin to spin as soon as the position input starts to change, thereby assisting M1 "immediately" and providing for a more robust control scheme. In particular, in the embodiment shown in FIG. 3, the velocity is computed as a derivative of the position input qcmd, as the latter is less noisy than q1' or q2' and also contains the desired direction to rotate. The f(q') block is a friction model (e.g., Coulomb friction, viscous friction) that is a function of velocity q', which here produces a boost torque input based on the velocity (speed and direction) of the position input qcmd'.

The embodiment of FIG. 3 may in some instances allow M1 to, on average, work harder than M2 when turning the output coupling 27. For example, it is possible that only when the error is "large" would there be significant torque assistance provided by M2. To mitigate such situations and thereby help increase reliability, the controller 33 may be programmable to change which motor subsystem is primary and which one or more are secondary. For example, the controller 33 may be programmable so that the torque input produced by the first compensator (e.g., position control) is instead provided to M2 while the torque input produced by the second compensator (e.g., impedance control) is provided to M1. In other words, the primary and secondary roles of the motor subsystems are swapped, so that M2 now acts as the primary as it receives the output of the first compensator (position control), while M1 becomes the secondary as it receives the output of the second compensator (impedance control.) The role of being the primary can be re-assigned round robin amongst all of motor subsystems, automatically over time as the multi-motor actuator ages, so that each one of the motor subsystems on average spends the same amount of time acting as the primary. This may even out the usage of the actuators and thereby help increase reliability of the overall system at a macro level.

Figure 4:
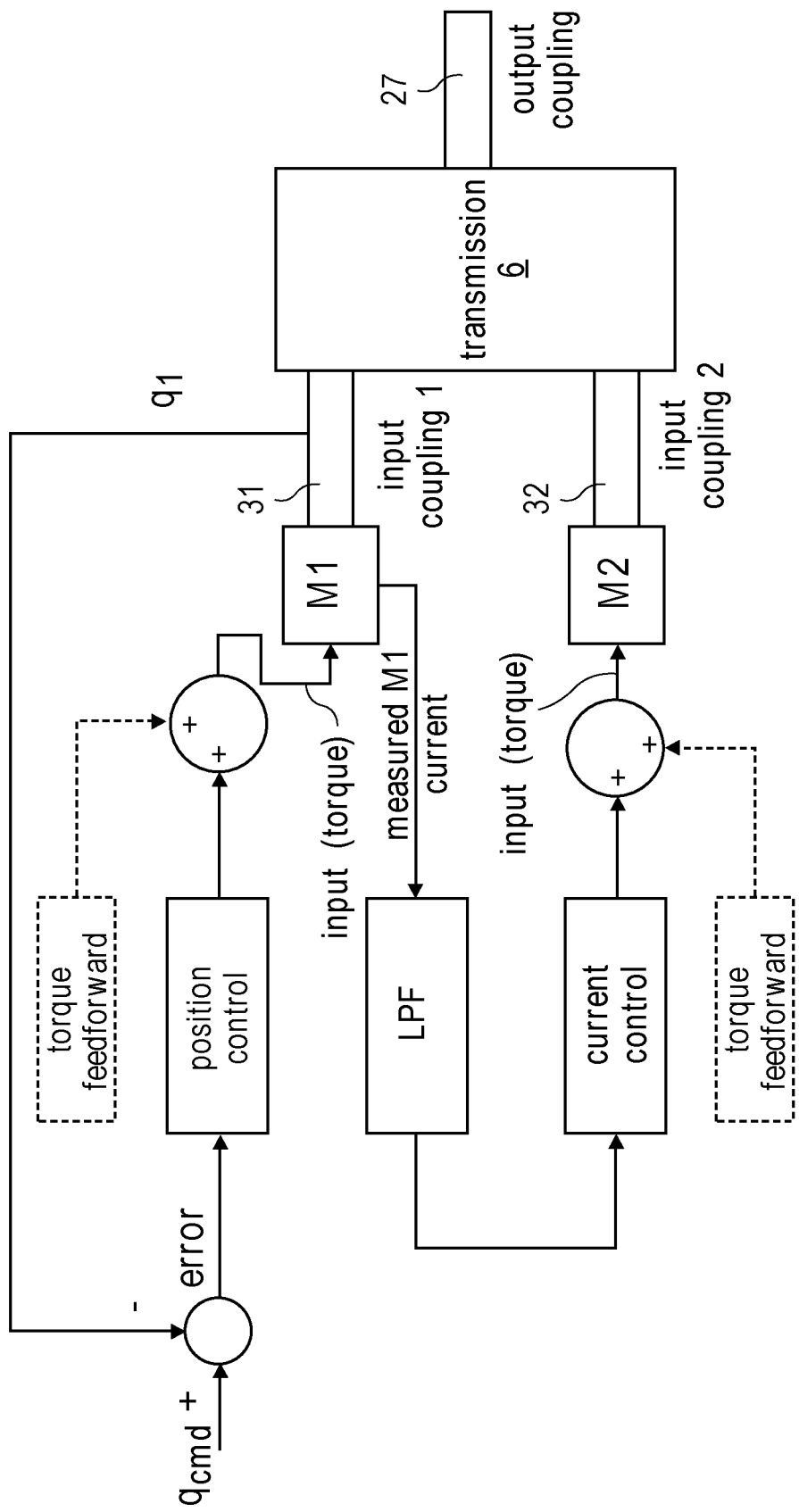
FIG. 4 is a block diagram of another embodiment of the controller.

In accordance with another embodiment of the invention, consistent with the desire to balance the workload between M1 and M2 at a micro level, or more evenly during a wider range of the position error, the block diagram of the controller 33 is offered as a solution, as shown in FIG. 4. Here, the primary motor subsystem M1 is operated in the same manner as in FIG. 3, namely within a position control servo loop, and whose torque input is produced by the first compensator (e.g., position control) as described above in connection with FIG. 3. In contrast however, the second motor subsystem M2 is now operated in a torque control servo loop (and not according to the impedance control law of FIG. 3), as follows. The controller 33 measures actual torque of the primary motor subsystem M1 (e.g., by measuring motor current of M1), and low pass filters (LPF) the measured torque and provides this as input to a second compensator (here, current control), which then produces the secondary motor subsystem M2 input. In the embodiment of FIG. 4, the first compensator (e.g., position control) may be a cascaded PID compensator, while the second compensator (e.g., current control) may be a proportional-integral, PI, compensator.

As with the embodiment of FIG. 3, the embodiment in FIG. 4 may also have an optional torque feedforward path (depicted in dotted line form) that includes a friction model configured to produce a torque-boost input to the motor subsystem M1 and/or the motor subsystem M2. Each torque boost is produced as a function of a velocity variable that is obtained from either the position input (qcmd), or feedback from the input coupling 31, input coupling 32, or the output coupling 27 (similar to what was described above in connection with FIG. 1).

For the embodiment of FIG. 4, note that M2 is under torque (current) control, so that there will not be energy buildup from M2 (which would usually occur due to the integral term) that could potentially fight against M1.

Figure 5:
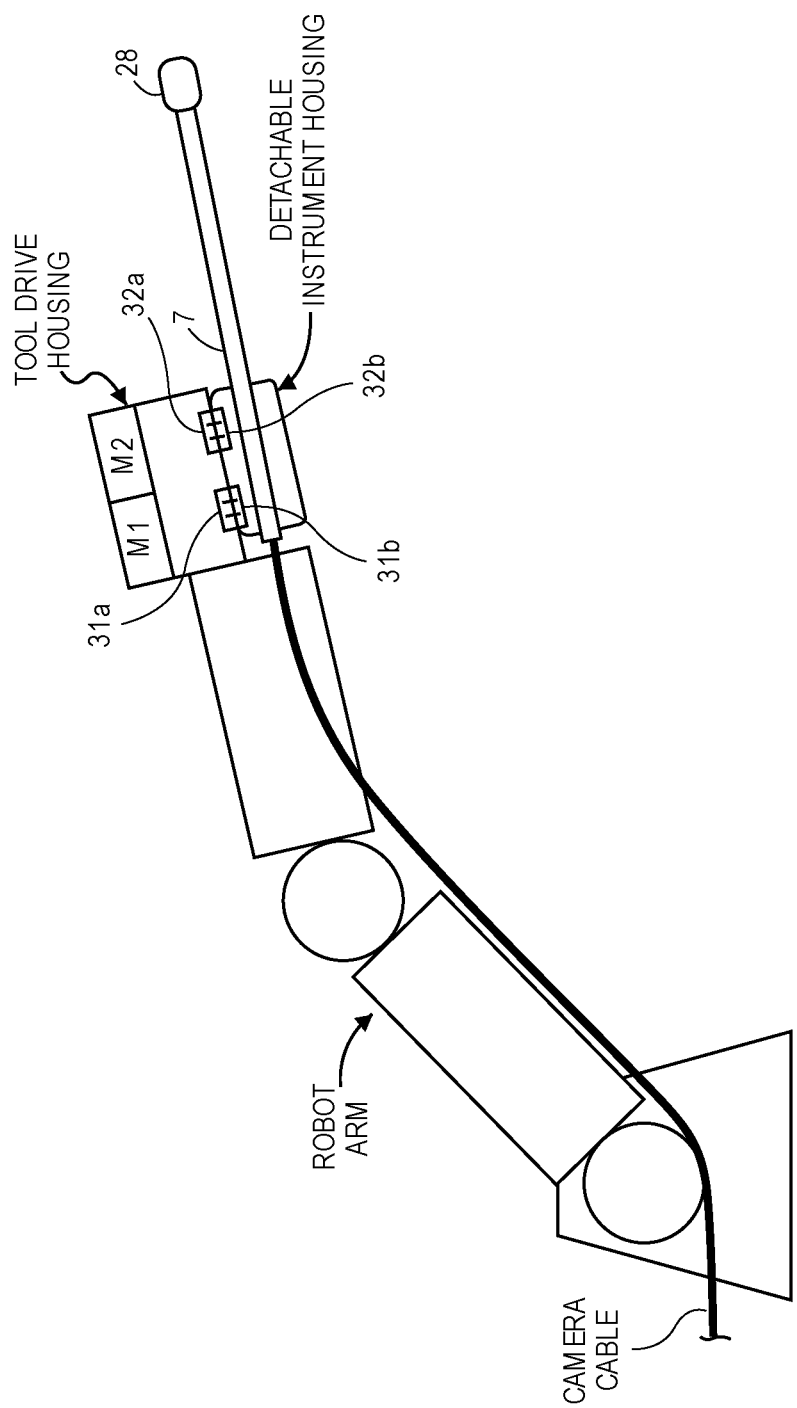
FIG. 5 depicts the multi-motor actuator as part of a tool drive on a surgical robotic arm, and a detachable robotic surgery tool that is coupled to the tool drive.

Turning now to FIG. 5, this figure depicts the multi-motor actuator having motor subsystems M1, M2 as part of a tool drive on a surgical robotic arm, that is encased within a tool drive housing. A detachable robotic surgery tool, having a detachable instrument housing in which the output coupling 27 with the coupled endoscope camera 8 as shown, is coupled to the tool drive. The instrument housing is separate from the tool drive housing and is detachable therefrom, to enable the same tool drive housing to be multi-purposed with different surgical instruments. In the embodiment shown in FIG. 5, the output coupling 31 has a first part 31a that is in the tool drive housing and is configured to mechanically and rigidly engage with a second part 31b that is in the detachable instrument housing (once the two housings have been fitted together.) For example, the first part 31a may be a drive disk or other coupling that is designed or configured to be engaged with the second part 31b being a mating drive disk (or other mating coupling.) A similar arrangement may be provided for the second output coupling 32, as having a first part 32a being for example a drive disk (or other coupling) that can be engaged and disengaged with a second part 32b being a mating drive disk (or other mating coupling.) In such an embodiment, a position encoder (not shown) that produces the needed feedback on the position of the input coupling 31 or the output coupling 32, or two position encoders for producing explicit feedback on both of the input couplings, 31, 32, may be housed within the tool drive housing. As explained above there is no need for obtaining explicit feedback from the instrument housing on the position of the output coupling 27.

FIG. 5 also reflects the understanding that the transmission 26 (depicted in FIG. 2) which serves to couple the input couplings 31, 32 to the output coupling 27, may also be composed of two parts, namely one part in the tool drive housing that couples the M1 drive coupling to the first part 31a of the input coupling 31, and another part in the instrument housing that couples the second part 31b of the input coupling 31 to the output coupling (with a similar arrangement provided for coupling the M2 drive coupling to the first part 32a of the input coupling 32, and for coupling the second part 32b of the input coupling 32 to the output coupling 27.)

The block diagram of FIG. 4 may be used to describe a method for controlling movement of a robotic surgery tool (that is coupled to the output coupling 27 of an actuator.) The method includes the following operations performed by the controller 33 (e.g., as a processor executing instructions stored in memory). A position error is determined based on a difference between i) a position input and ii) a position feedback, wherein the position feedback is on a first input coupling, a second input coupling or the output coupling of the actuator. As described above in connection with FIG. 2, the first and second input couplings are rotatably coupled to simultaneously drive and rotate the output coupling, and wherein a first motor subsystem drives the first input coupling in accordance with a first motor subsystem input and a second motor subsystem drives the second input coupling in accordance with a second motor subsystem input. The controller produces the first motor subsystem input in accordance with a position control law and based on providing the position error as input to a first compensator (position control.) The controller is also measuring torque of the first motor subsystem, and low pass filtering the measured torque which is then input to a second compensator (current control), to produce the second motor subsystem input. The controller may also produce a torque boost that increases the first or second motor subsystem input, wherein the torque boost is produced as a function of a velocity variable that is obtained from one of the position input, feedback on the first output coupling, feedback on the second output coupling, or feedback on the output coupling. Note that any feedback from a particular coupling, as the expression is used here, may be a sensed value produced by a directly related sensor (e.g., a velocity sensor that is sensing rotation velocity of a coupling and producing a velocity value directly, a position sensor or encoder producing a position value directly), or it may be a calculated value that has been derived using a mathematical relationship with another type of sensor (e.g., taking the time derivative of position values produced by a position sensor to calculate a velocity value.)

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For instance, while FIG. 2 shows the output coupling 27 as being part of an endoscope, the output coupling 27 may alternatively be part of a different robotic surgery tool. The description is thus to be regarded as illustrative instead of limiting.

What is claimed is:

1. A control system for an end effector that is to be attached to a surgical robotic arm, comprising:
a first motor and a second motor to be coupled to the end effector to rotatably drive an output coupling so that torques produced by the first motor and the second motor, respectively, are summed at the output coupling, wherein the motors are to be driven in accordance with a first motor command and a second motor command; and
a controller configured to generate the first motor command using a position error input, and configured to generate the second motor command using the position error input to assist the first motor in meeting a torque demand from the end effector.

2. The control system of claim 1, wherein the controller is configured to determine the position error input as a difference between a position input command and a position feedback from the first motor.

3. The control system of claim 1, wherein the controller comprises a friction model that is configured to generate a torque boost to one or more of the first motor or the second motor, and wherein the torque boost is generated as a function of a velocity variable that is obtained from one of: a position input command, feedback from a first input coupling coupled to the first motor, feedback from a second input coupling coupled to the second motor, or feedback from the output coupling.

4. The control system of claim 1, wherein the first motor and the second motor are coupled to the output coupling to rotatably drive the output coupling through a transmission.

5. The control system of claim 4, wherein each of the first motor and the second motor have respective torque ratings insufficient to drive the output coupling by itself through the transmission.

6. The control system of claim 4, wherein the controller produces the second motor command by measuring motor current of the first motor and then low pass filtering the measured motor current before performing a control system compensation algorithm to produce the second motor command.

7. The control system of claim 1, wherein the controller is configured to change which of the first motor or the second motor rotatably drives the output coupling in accordance with the first motor command.

8. The control system of claim 1, further comprising:
an endoscope camera coupled to the output coupling; and
an endoscope camera cable having one end coupled to the endoscope camera and extending through a hollow in the output coupling, wherein the endoscope camera cable twists and resists rotation of the output coupling.

9. The control system of claim 1, wherein the controller generates the first motor command at a lower bandwidth than the second motor command.

10. A control system, comprising:
a first motor and a second motor to be coupled to an effector that is to be attached to a surgical robotic arm in such a way that the first motor and the second motor rotatably drive an output coupling so that torques produced by the first motor and the second motor, respectively, are summed at the output coupling, wherein the motors are to be driven in accordance with a first motor command and a second motor command; and
a controller configured to
generate the first motor command using a position error input,
measure torque of the first motor, and
generate the second motor command based on the measured torque.

11. The control system of claim 10, wherein the controller comprises a friction model that is configured to generate a torque boost to one or more of the first motor or the second motor, and wherein the torque boost is generated as a function of a velocity variable that is obtained from one of: a position input command, feedback from a first input coupling coupled to the first motor, feedback from a second input coupling coupled to the second motor, or feedback from the output coupling.

12. The control system of claim 10, wherein the first motor and the second motor are coupled to the output coupling through a transmission.

13. The control system of claim 12, wherein each of the first motor and the second motor have respective torque ratings insufficient to drive the output coupling by itself through the transmission.

14. The control system of claim 12, wherein the transmission comprises a first part that is housed in a tool drive housing, and a second part that is housed in an instrument housing separate from the tool drive housing and that is detachable therefrom.

15. The control system of claim 10, wherein the controller is configured to produce the second motor command by measuring motor current of the first motor and then low pass filtering the measured motor current before performing a control system compensation algorithm to produce the second motor command.

16. The control system of claim 10, wherein the controller generates the first motor command at a lower bandwidth than the second motor command.

17. The control system of claim 10 further comprising:
an endoscope camera coupled to the output coupling; and
an endoscope camera cable having one end coupled to the endoscope camera and extending through a hollow in the output coupling, wherein the endoscope camera cable twists and resists rotation of the output coupling.

18. A method for use in a surgical robotic system, comprising:
operating a first motor subsystem coupled to an end effector, wherein operating the first motor subsystem includes generating, by a controller, a first motor command based on a position error input to drive the first motor subsystem; and
operating a second motor subsystem coupled to the end effector, wherein operating the second motor subsystem includes generating, by the controller, a second motor command based on the position error input or based on feedback from the first motor subsystem to drive the second motor subsystem, wherein the first motor subsystem and the second motor subsystem are coupled to the end effector so as to rotatably drive an output coupling so that torques produced by the first motor subsystem and the second motor subsystem, respectively, are summed at the output coupling.

19. The method of claim 18, wherein the second motor command is generated by the controller while operating in a torque control servo loop with the second motor subsystem and the first motor command is generated by the controller while operating in a position control servo loop with the first motor subsystem.

20. The method of claim 18, wherein the feedback from the first motor subsystem includes measured torque of the first motor subsystem, and wherein the second motor command is generated based on the measured torque.

\* \* \* \* \*